United States Patent [19]

Anderson

[11] Patent Number: 4,536,475
[45] Date of Patent: Aug. 20, 1985

[54] PLANT VECTOR
[75] Inventor: David M. Anderson, Duarte, Calif.
[73] Assignee: Phytogen, Pasadena, Calif.
[21] Appl. No.: 432,842
[22] Filed: Oct. 5, 1982
[51] Int. Cl.³ .......................... C12N 15/00; C12N 1/00
[52] U.S. Cl. .................................. 435/172.3; 435/317; 935/30
[58] Field of Search ...................... 435/172, 317, 172.3; 935/30

[56] References Cited

U.S. PATENT DOCUMENTS 4,407,956 10/1983 Howell ................................ 435/317

OTHER PUBLICATIONS

Howell et al., Nature, vol. 293, pp. 483–486, Oct. 8, 1981.
Hohn et al., Gene, vol. II, pp. 21–31, (1980).
Depicker et al., Plasmid, vol. 3, pp. 193–211, (1980).
McKnight et al., Cell, vol. 25, pp. 385–398, Aug. 1981.
Otten et al., Mol. Gen. Genet., vol. 183, pp. 209–213, (1981).
Zambryski et al., Science, vol. 209, pp. 1385–1391, (1980).
Beuckeleer et al., Mol. Gen. Genet., vol. 183, pp. 283–288.

Primary Examiner—Alvin E. Tanenholtz
Attorney, Agent, or Firm—Christie, Parker & Hale

[57] ABSTRACT

There are provided herewith vector precursors and vectors based on Pst I cleaved left and right border fragments of the T region of the Ti plasmid *Agrobacterium tumefaciens* strain of C58 interligated and ligated into the Pst I site of plasmid pBR322. Antibiotic resistance gene sequence is used to establish vector expression and presence in host cells.

7 Claims, 10 Drawing Figures

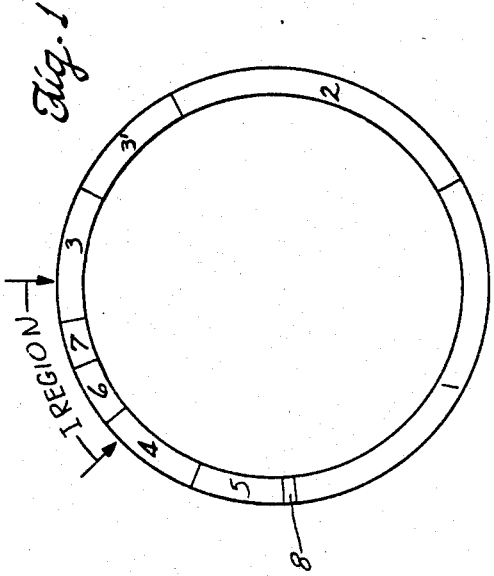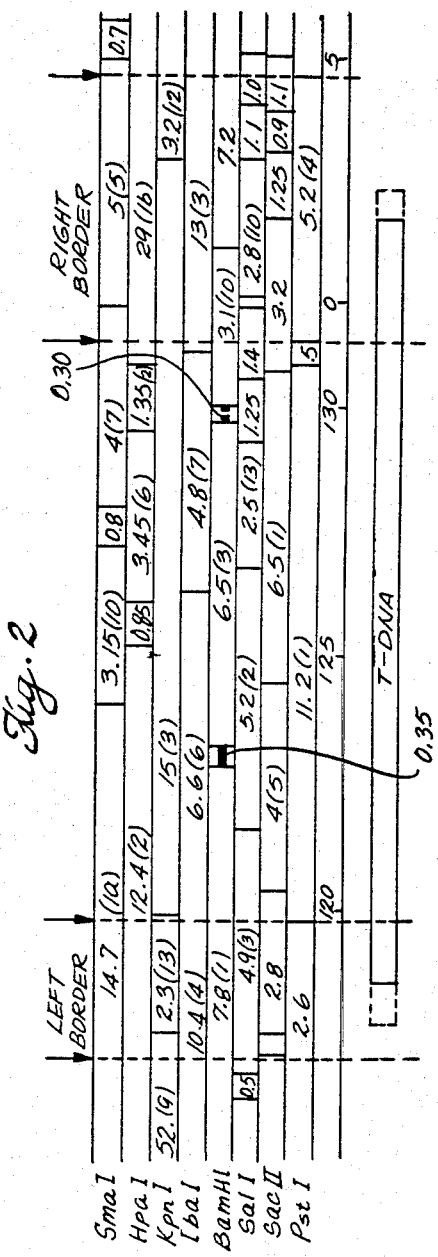

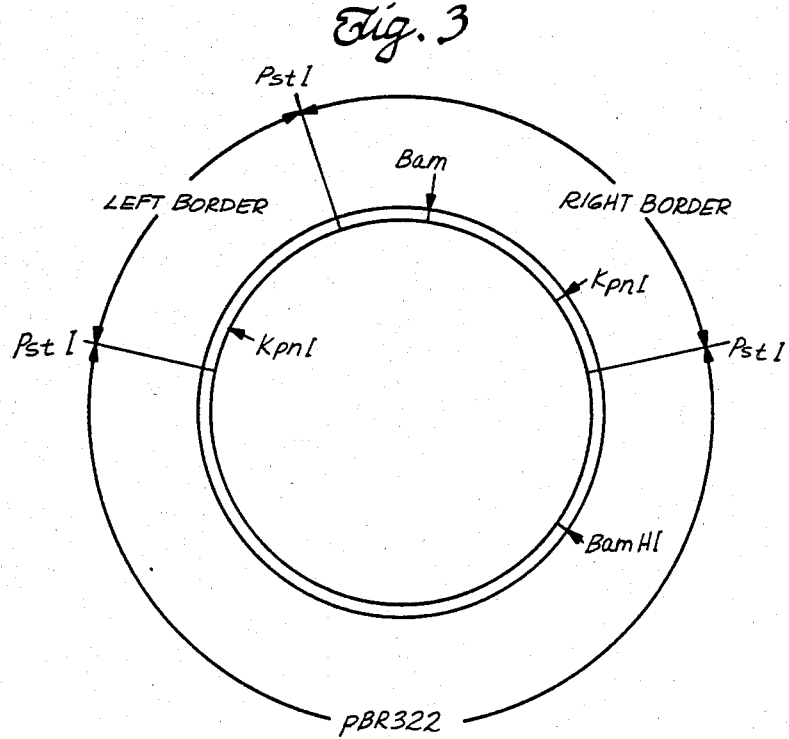
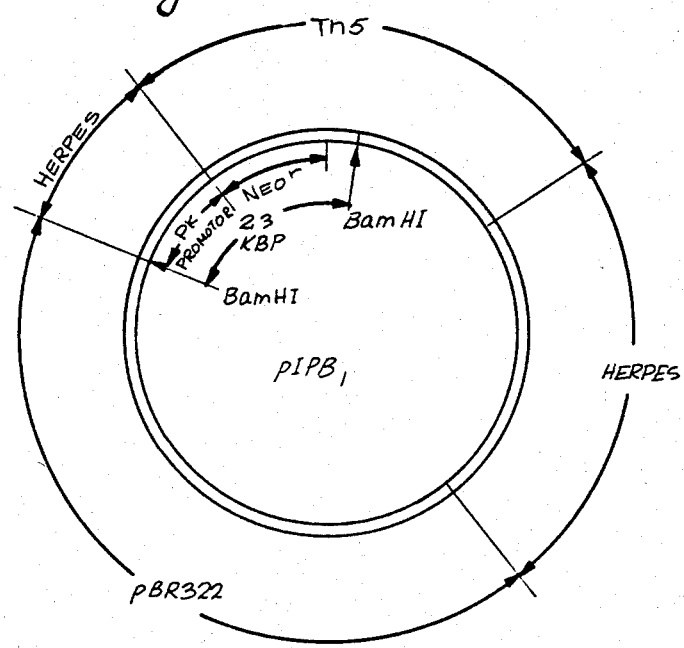

PLANT VECTOR

BACKGROUND OF THE INVENTION

With the development of modern molecular biology, it is now possible to isolate individual genes from organisms virtually at will. This has placed within the realm of possibility the genetic manipulation of economically important agricultural plants. Desirable goals include the development of plant varieties with new traits such as improved nutritional quality, productivity, disease resistance, and drought and salinity tolerance. The major obstacle to the realization of these goals is lack of an agent or "vector" for the stable introduction of foreign genes into plant cells.

Bacteria of the genus Agrobacterium have the capacity to induce crown gall tumors in dicotyledonous plants. The genetic determinant responsible for this tumorous transformation is carried by large plasmids, called Ti plasmids, present within these bacteria. This is a natural system for the transformation of plant cells, and it has been shown to be due to the stable integration of at least a part of the Ti plasmid (the so-called T region) into the host plant cell genome. The T region DNA sequences which occur covalently attached to plant DNA in transformed cells are the same in different tumor lines. This means that the DNA sequences responsible for integration of the T region are precisely defined.

It would be desirable to provide a plant vector having the functional portions of the T region DNA sequences but incapacitated in respect of its ability to induce plant tumor formation, and this is the subject of the present invention.

SUMMARY OF THE INVENTION

There is provided in accordance with the present invention, novel vectors, a precursor thereof, and their method of preparation.

The vectors provided in accordance with the present invention are formed from a vector precursor comprising the Pst I cleaved left and right border fragments of the T region of the Ti plasmid *Agrobacterium tumefaciens* strain of C58 which are interligated and ligated into the Pst I site of plasmid pBR322. A vector is formed by ligating into the border fragments a promoter for gene transcription, a bacterial gene for selection, and, as desired, any foreign gene to be inserted into the plant cell is also ligated into the border fragments. The preferred bacterial gene is one resistant to neomycin analogues such as kanamycin, G-418 and the like.

One such vector comprising the left and right border fragments of the T region of the Ti plasmid *Agrobacterium tumefaciens* strain of C58 ligated in proper orientation to the Pst I site of the plasmid pBR322, contains within the right border segment at the BamHI site the thymidine kinase promoter and adjacent neomycin resistance gene. By proper orientation, there is meant in the orientation which existed in the T region.

Another vector comprises a first segment comprising the Pst I left and right border sequences of the T region of the Ti plasmid *Agrobacterium tumefaciens* strain C58 ligated in proper orientation to the Pst I site of the plasmid pBR322 and in which there is contained within the right border segment at the BamHI site, thymidine kinase promoter and adjacent neomycin resistance gene ligated into the Hpa I site of the cauliflower mosaic virus cloned into PBR322 at blunted Kpn I sites of the right border sequence.

The general process for vector formation comprises isolating from the Ti plasmid *Agrobacterium tumefaciens* strain of C58, right- and left-hand border sequences generated by XbaI cleavage. The right-hand and left-hand border sequences are cleaved with Pst I, combined in the same orientation as in the Ti plasmid, and ligated into the Pst I site of the plasmid pBR322 at a temperature of about 30° C. or less. There is then introduced to the border sequences an antibiotic gene sequence and an adjacent eukaryotic transcription promoter sequence. To this base vector there may be, as desired, added a DNA sequence capable of serving as an origin of DNA replication for the vector. Either vector can serve to introduce foreign gene information to a plant cell.

THE DRAWINGS

FIG. 1 is the restriction map of the nopaline plasmid pTiC58 with the restriction endonuclease XbaI. The total molecular weight of the plasmid is $1.32 \times 10^8$ daltons. Restriction fragments are indicated by number. The T region, which integrates within the host plant cell genome, is shown.

FIG. 2 is the restriction map of the T-DNA of nopaline Ti plasmid pTiC58. The respective enzymes are listed at the left, and the resulting cleavage products are shown in blocks. The number of each fragment (parentheses) and the molecular weight are given. The mpa is calibrated in units based on molecular weight: 1 map unit (T) equals 1 Mdal (132 T for the entire pTiC58 plasmid), with the SmaI restriction site on the right border of the T region taken as point zero. The actual T region is indicated at the bottom of the figure. The arrows indicate the Pst I fragments which contain the left and right border positions, and which were cloned into the plasmid pBR322.

FIG. 3 depicts the structure of the plasmid resulting from the ligation of the left and right border-containing Pst I fragments into pBR322. Additional cleavage sites for the restriction endonucleases BamHI and KpnI are shown.

FIG. 4 depicts a restriction map of the plasmid pIPB$_1$ constructed from known plasmids. The position of the neomycin resistance gene (Neo$^r$) within the herpes thymidine kinase gene (TK promoter) is indicated. The 2.3 kilobase pair (2.3 KBP) BamHI fragment including the TK promoter and the neomycin resistance gene is shown. One can obtain pIPB$_1$ from Barbara Wold at California Institute of Technology.

DETAILED DESCRIPTION

Figure 5:
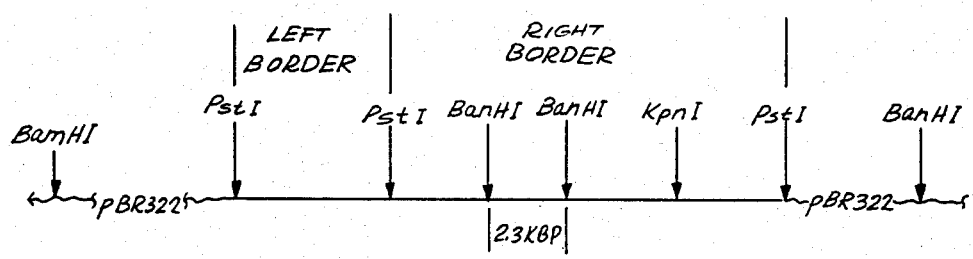
FIGS. 5 and 6 illustrate the ligation of the 2.3 kilobase pair into the right border region to form Plant Vector I.

The present invention is directed to the construction of a variety of recombinant plasmids to provide for the first time a means of obtaining the stable integration and expression of foreign genes into plant cells of both monocotyledonous and dicotyledonous plants, without the necessity of inducing plant cell tumors.

Methods and compositions are provided in accordance with the instant invention to enable the genetic transformation of eukaryotic organisms to provide diverse genotypical capability in any eukaryotic cell and the development of genotypically diverse plants.

In accordance with the invention, a recombinant plasmid is constructed, which includes a bacterial plasmid into which are ligated the border sequences from the T region of the Ti plasmid which enables integration into the plant cell genome, while genes responsible for Ti plasmid-induced tumor formation are specifically rendered ineffective. The bacterial plasmid allows for positive selection of transformed plant cells. A bacterial gene conferring antibiotic resistance is ligated into the vector within the left or right border segments.

To insure that expression of the antibiotic resistance gene occurs in modified plant cells, a eukaryotic transcription promoter sequence is ligated next to the bacterial antibiotic resistance gene. Any foreign gene can then be ligated into the vector between the border sequences and near the antibiotic resistance gene. Plant cells can be treated with the vector, and transformants can be selected by their resistance to the antibiotic and its analogues. preferred antibiotics are kanamycin and G-418, an antibiotic manufactured by Schering Corp.

Key components needed for the stable introduction of foreign genes into plant cells are DNA sequences capable of promoting integration of genes into the host plant cell genome; DNA sequences which can function as promoters of transcription of the gene introduced; and a method to select transformed cells DNA sequences which can serve as origins of replication for the vector and associated genes following introduction into a recipient plant cell would also be useful.

There is utilized in accordance with this invention a portion of the T region of the Ti plasmid of *Agrobacterium tumefaciens* as the basis for the construction of such a vector. The vector construction will now be detailed in terms of isolation of the Ti plasmid T region border fragments; ligation of the border fragments together in the proper orientation into a plasmid for convenient replication in *E. coli*; addition to the border fragments of a bacterial gene for kanamycin resistance containing the promoter region of a eukaryotic gene; addition of DNA sequences (the CaMV genome) capable of serving as an origin of DNA replication for the vector in plant cells; and demonstration of the efficacy of this vector in the transformation of plant cells.

With reference now to FIG. 1, naturally occurring cells of nopaline crown gall tumor inducing *Abrobacterium tumefaciens* strain C58 (pTiC58) were grown in a liquid medium of yeast extract and bactopeptone (YEB) and the Ti plasmid isolated by lysis of the cells followed by CsCl centrifugation. The Ti plasmid obtained from this strain has a molecular weight of about $1.32 \times 10^8$ daltons, or about $2 \times 10^5$ nucleotide pairs. The T region itself is a defined plasmid segment of about $1.5 \times 10^7$ daltons, or about $2 \times 10^4$ nucleotide pairs. The plasmid was cleaved by the restriction endonuclease XbaI to generate 9 fragments of defined molecular weight. They range in size from about $6.4 \times 10^4$ NTP (fragment 1) to $1.5 \times 10^3$ NTP (fragment 8). Segments 3 and 3' differ, but are about the same size. Contiguous XbaI fragments 4, 6, 7 and 3 include within them all of the T region. In tumors induced by this plasmid, the junction between plant and T region DNA is precisely defined. These so-called border sequences are located in XbaI fragment 4 ($10.4 \times 10^6$ daltons) for the left border, and XbaI fragment 3 ($13 \times 10^6$ daltons) for the right border.

With reference to FIG. 2, the left border region was then localized more precisely to within a $4 \times 10^3$ NTP Pst I fragment within XbaI fragment 4 ($2.6 \times 10^6$ daltons). To isolate the left border fragment, 3 μg of total Ti plasmid DNA was cleaved with the restriction endonuclease XbaI and separated by electrophoresis on 0.8% agarose gels. Each of the individual bands was cut out of the gel and isolated by electroelution. Band 4 was then cleaved with the restriction endonuclease Pst I and ligated directly into the Pst I site of the plasmid pBR322 from *E. coli* vector. *E. coli* strain HB101 was transformed, and tetracycline-resistant, ampicillin-sensitive (Tet$^r$Amp$^s$) colonies were selected. Recombinant plasmids containing the proper $4.3 \times 10^3$ NTP insert were identified by restriction endonuclease digestion. The left border Pst I fragment was verified by the presence of restriction endonuclease Sac II and restriction endonuclease KpnI fragments of proper length.

The right border fragment was isolated in the same manner. XbaI fragment 3, which is actually a double band, was cleaved with Pst I to a fragment of about $5.2 \times 10^6$ daltons in size, ligated into the Pst I site of pBR322, and used to transform HB101. Tet$^r$Amp$^s$ colonies were selected, and transformants with the proper Pst I insert were identified by restriction endonuclease digestion. As opposed to fragment 3', the right border Pst I fragment is about $8.6 \times 10^3$ NTP and contains, with reference to FIG. 2, characteristic SmaI, BamHI and KpnI restriction endonuclease sites.

The key to this invention is the ability to utilize the left and right border sequences for integration into a host plant cell genome, while eliminating the undesirable trait of oncogenicity. This was achieved by joining the left and right border sequences, while eliminating the intervening T region sequences which are unnecessary for integration.

The left and right border-containing plasmids were mixed together in equimolar amounts, cleaved with Pst I to release their respective left and right border sequences, and ligated together at a relatively high concentration (100 μg/ml), a condition which tends to favor the formation of multimolecular units. This DNA was used to transform *E. coli* strain Hb101. The cells were plated and incubated overnight at about 30° C. This temperature, or a lower temperature, was necessary to obtain the required large plasmids during transformation. After religation, Tet$^r$Amp$^s$ colonies were selected and screened for plasmids with multiple inserts (i.e., with a total size of at least $1.7 \times 10^4$ NTP). These were cleaved with Pst I to identify those with both a left and a right border fragment. These clones were then further screened with the enzymes Kpn I and Sac II to identify those clones which contained the left and right border fragments together in the proper orientation. The desired and selected plasmid is illustrated in FIG. 3.

Addition to the border fragments of a bacterial gene for kanamycin resistance containing the promoter region of a eukaryotic gene was provided to establish a mechanism for the positive selection of transformed plant cells. Plant cells are sensitive to the antibiotic kanamycin and/or its analogues such as G-418. The kanamycin resistance gene originally obtained from the bacterial transposable element Tn5 was selected. In order to insure transcription of this gene in eukaryotic cells, it was necessary to place a eukaryotic transcription promoter on the 5' end of the gene. For convenience, this was provided by the Herpes Simplex virus thymidine kinase gene. With reference to FIG. 4, a plasmid (pIPB$_1$) which includes the neomycin resistance gene (Neo$^r$) cloned into the thymidine kinase gene adjacent the promoter, and an *E. coli* strain containing this plasmid was grown in a nutrient broth. The cells were lysed and the plasmid isolated by CsCl centrifugation. The plasmid was cleaved with the restriction endonuclease BamHI, which liberates a $2.3 \times 10^3$ NTP DNA fragment which contains the thymidine kinase promoter (TK promoter) and all of the neomycin resistance gene (Neo$^r$). This fragment was isolated by electrophoresis in a 1% agarose gel, followed by electroelution.

Figure 6:
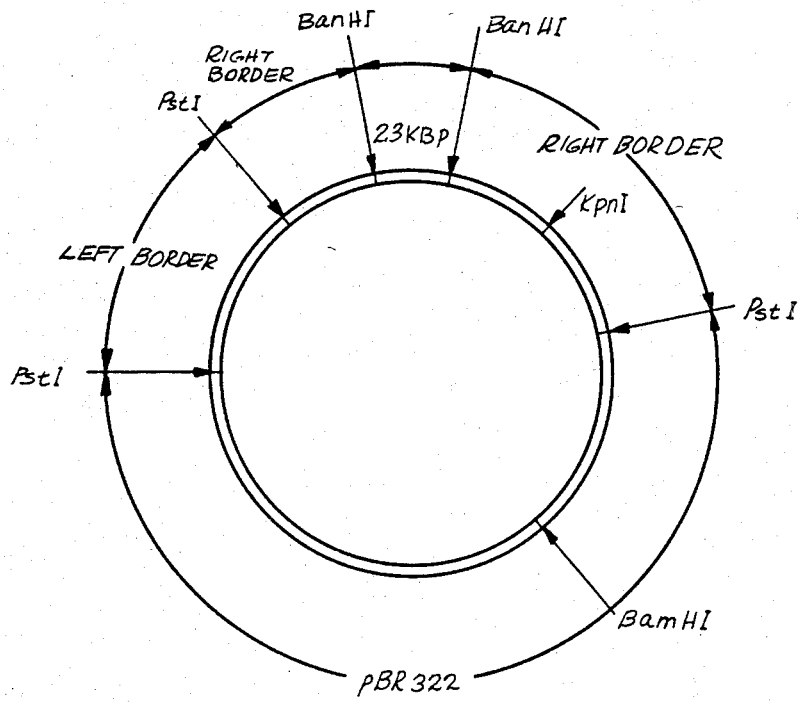

With reference to FIG. 5, the left and right border-containing clone was then cleaved with BamHI. This enzyme cleaves the clone twice; once in the right border fragment, and once within the pBR322 sequence. One microgram of the DNA was ligated with 200 ng of the neomycin resistance gene containing BamHI fragment (TK promoter-Neo$^r$) at a final DNA concentration of 100 μg/ml, and used to transform *E. coli* strain HB101. Tet$^r$Amp$^s$ colonies were screened for the presence of the neomycin resistance fragment in the right border sequence only, by restriction endonuclease digestion. Since it carries its own promoter (TK promoter), this fragment can be inserted in either orientation. This plasmid is termed herein "Plant Vector I," and is shown in FIG. 6.

Experiments in other systems have suggested that when foreign DNA is introduced into a recipient cell, the probability of an integration event occurring is directly related to the number of foreign DNA molecules introduced. There were therefore added DNA sequences to Plant Vector I to serve as an origin of DNA replication for the vector in a recipient cell. This is to provide the vector with two advantages. First, it can be maintained in a transfomed cell line without an integration event occurring. Second, it allows the vector to amplify within the recipient cell, thereby increasing the opportunity for integration to occur.

Figure 7:
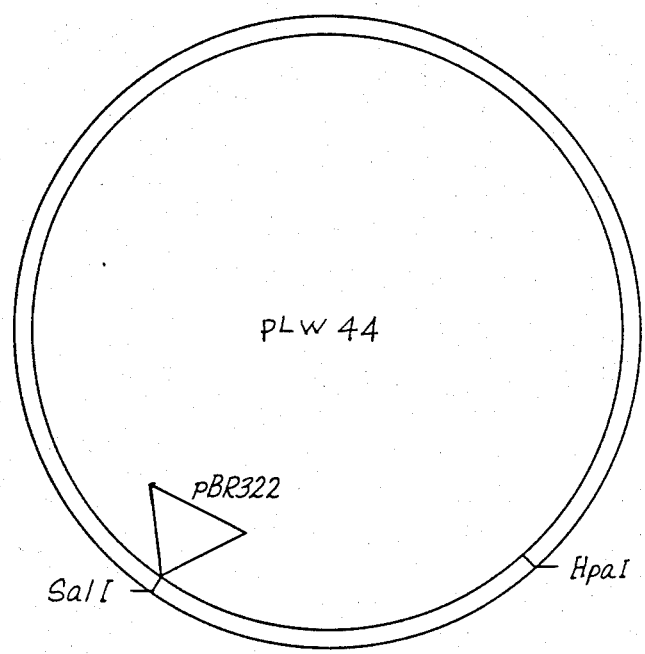
FIG. 7 illustrates the cauliflower mosaic virus cloned in plasmid pBR322 (pLW414), showing the position of the HpaI site.
Figure 8:
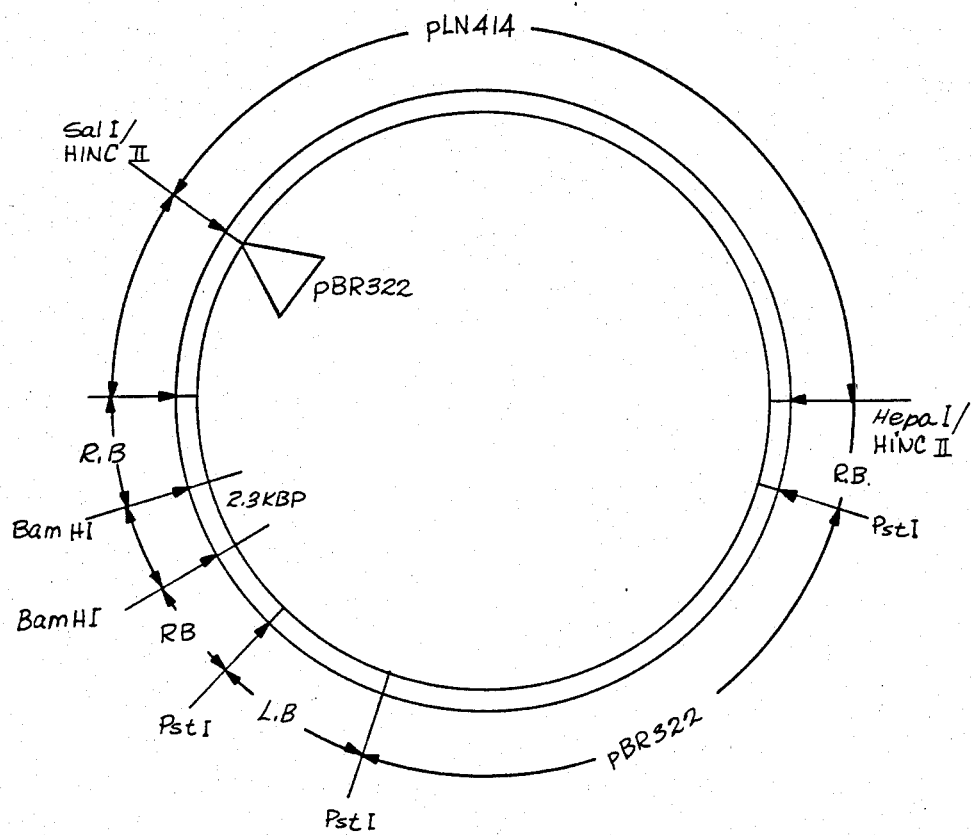
FIG. 8 illustrates Plant Vector III, formed by bluntend ligating PLW414 cleaved at the HpaI site to Plant Vector I, blunt-ended after cleavage at the KpnI site in the right border segment, where "LB" means left-hand border sequence, and "RB" means right-hand border sequence.

Although other eukaryotic origins of replication may be introduced, there was, with reference to FIG. 7, selected for convenience the cauliflower mosaic virus (CaMV) genome cloned in pBR322 (plasmid PLW414) as a DNA replication origin source. PLW414 (provided by S. Howell of UCSD) contains the entire CaMV genome cloned in the Sal I site of pBR322. Thus, this plasmid is Amp$^r$Tet$^s$. PLW414 was grown in L broth, the plasmid isolated by CsCl centrifugation, and 1 μg cleaved at its single HpaI site, which cleaves to leave non-overhanging or "blunt" ends. One μg of Plant Vector I was partially cleaved at a single KpnI site, and the ends made non-overhanging by digestion with S1 nuclease. The DNAs were mixed, extracted with phenol to remove proteins, ethanol precipitated, and resuspended in 20λ of ligation buffer. The DNA segments were blunt-end ligated together, used to transform HB101, and plated on L broth plates at about 30° C. containing both tetracycline and ampicillin. Only those transformants containing PLW414 ligated in Plant Vector I were viable. This was verified by restriction endonuclease analysis of the resultant clones. This plasmid is termed herein "Plant Vector III," and is shown in FIG. 8.

Plant Vector I and Plant Vector III have been tested in monocotyledonous (barley) and dicotyledonous (tobacco) plants. In both cases, assay for the presence of the given vector within recipient plant cells, and its concomitant expression, has been the acquisition of resistance to the antibiotic kanamycin by plant cells previously sensitive to it. In the trials, the vector DNA was introduced into isolated protoplasts by liposome mediated fusion.

Tobacco protoplasts were isolated from leaves, while barley protoplasts were obtained from apical meristem and base region tissue. Protoplasts ($10^6$/trial) were incubated in an isotonic sucrose buffer containing Plant Vector I or Plant Vector III encapsulated in liposomes and at a final ratio of about $10^5$ liposomes per cell. Protoplasts were incubated for about 30 minutes, washed, and plated on agar containing about 50 μg/ml kanamycin sulfate. Under these conditions, less than 1% of the control protoplasts (untreated vector) underwent cleavage, while up to 5% of the treated protoplasts cleaved and produced cell massess with as many as 16 cells. These experiments demonstrated that the vector was retained and functional in a measurable fraction of the treated protoplast population.

In the above procedure, the YEB medium was 0.5% Bacto-beef extract, 0.1% Bacto-yeast extract, 0.5% peptone, and 0.5% sucrose in 0.002M MgSO$_4$ (pH7.2).

The Ti plasmid pTiC58 was isolated from *Abrobacterium tumefaciens* strain C58 as described by T. C. Currier and E. W. Nester, *Analytical Biochemistry*, Vol. 76, 431–441 (1976).

The restriction enzymes were obtained from Calbiochem, New England Biolabs, or Bethesda Research Laboratories, and used in accordance with the conditions recommended by the supplier.

L Broth (LB) was 1% Bacto-tryptone, 0.5% yeast extract, 0.5% NaCl, 0.2% casamino acids, pH 7.2. LB plates were LB plus 15% Bacto-agar. Plates or broth were supplemented with ampicillin (50 μg/ml) or tetracycline (20 μg/ml) where appropriate.

Figure 9:
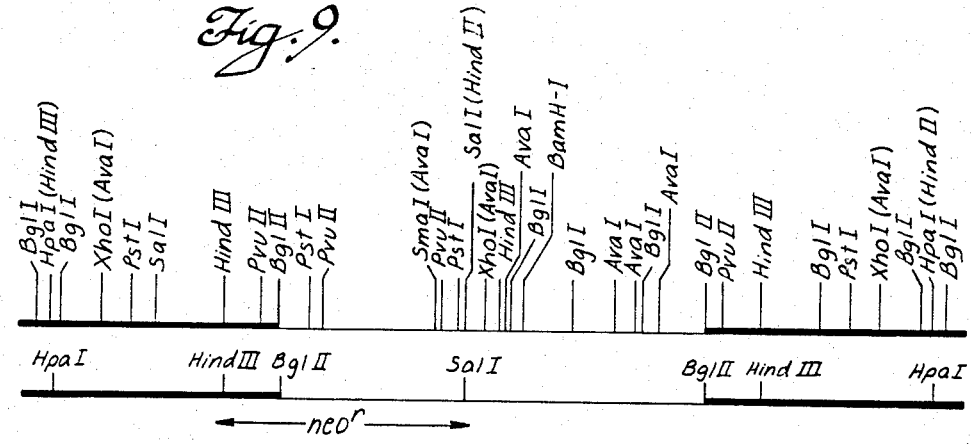
FIG. 9 is the restriction endonuclease map of the essential segment of Tn5, the source being Rothstein et al, Cell 19, 795–805 (1980).
Figure 10:
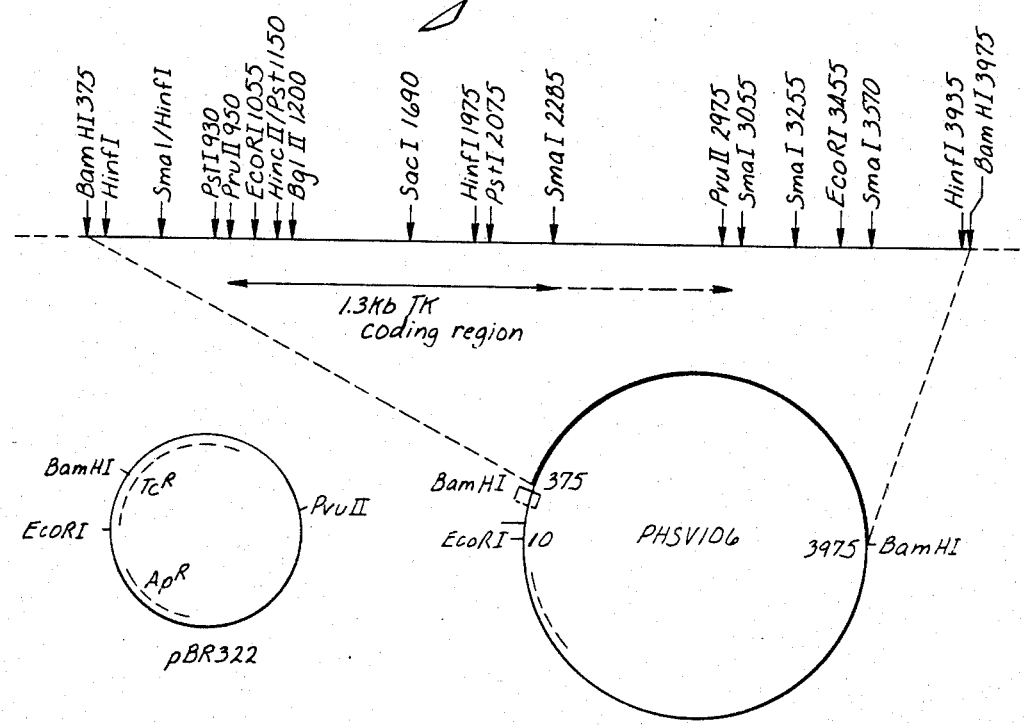
FIG. 10 shows, with reference to pBR322, the restriction enzyme segment of pHSV106, showing the BamHI and EcoRI sites.

The recombinant plasmid pIPB$_1$ used was provided by Dr. B. Wold of the California Institute of Technology. It was constructed using conventional techniques by splicing the 2.8 kilobase pair BglII fragment of the bacterial transposon Tn5 into the BglII site of a plasmid equivalent to pHSV106. pHSV106 is available from Bethesda Research Laboratories. Restriction endonuclease maps of the important regions of these DNAs are reproduced in FIGS. 9 and 10.

What is claimed is:

1. A vector precursor comprising the Pst I cleaved left and right border fragments of the T region of the Ti plasmid *Agrobacterium tumefaciens* strain of C58 interligated and ligated into the Pst I site of plasmid pBR322.

2. A vector comprising the Pst I-cleaved left and right border fragments of the T region of the Ti plasmid *Agrobacterium tumefaciens* strain of C58 ligated to the Pst I sites of the plasmid pBR322 and in which there is contained within the border segments a eukaryotic transcription sequence next to an antibiotic resistance gene sequence.

3. A vector as claimed in claim 2 in which there is ligated into the border sequence a gene sequence for DNA replication for the vector in plant cells.

4. A vector comprising the Pst I cleaved left and right border fragments of the T region of the Ti plasmid *Agrobacterium tumefaciens* strain of C58 ligated to the Pst I sites of the plasmid pBR322 in proper orientation and in which there is contained within the right border segment at the BamHI site the thymidine kinase promoter and neomycin resistance genes.

5. A vector comprising a first segment comprising the Pst I cleaved left and right border sequences of the T region of the Ti plasmid *Agrobacterium tumefaciens* strain C58 ligated to the Pst I sites of the plasmid pBR322 in proper orientation and in which there is contained within the right border segment at the BamHI site thymidine kinase promoter and neomycin resistance genes ligated into the Hpa I site of the cauliflower mosaic virus at blunted Kpn I sites of the right border sequence.

6. A process for vector formation which comprises:
(a) isolating from the Ti plasmid *Agrobacterium tumefaciens* strain of C58 right- and left-hand border sequences generated by XbaI cleavage;
(b) cleaving the right-hand and left-hand border sequences with Pst I;
(c) combining the Pst I cleaved left- and right-hand border sequences in the same orientation as in the Ti plasmid into the Pst I site of the plasmid pBR322 at a temperature of about 30° C. or less; and
(d) introducing to the border sequences an antibiotic gene sequence and an adjacent eukaryotic transcription promoter sequence.

7. A process as claimed in claim 6 in which a DNA sequence capable of serving as an origin of DNA replication for the vector is inserted into the border sequences.

* * * * *